United States Patent [19]

Fodge et al.

[11] Patent Number: 5,429,828
[45] Date of Patent: Jul. 4, 1995

[54] HEMICELLULASE SUPPLEMENT TO IMPROVE THE ENERGY EFFICIENCY OF HEMICELLULOSE-CONTAINING ANIMAL FEED

[75] Inventors: Douglas W. Fodge; David M. Anderson, both of Rockville, Md.

[73] Assignee: Chemgen Corporation, Gaithersburg, Md.

[21] Appl. No.: 912,675

[22] Filed: Jul. 14, 1992

Related U.S. Application Data

[63] Continuation of Ser. No. 529,327, May 29, 1990, abandoned.

[51] Int. Cl.$^6$ ................................. A23L 1/10
[52] U.S. Cl. .......................... 426/18; 426/28; 426/44; 426/53; 426/61; 426/64
[58] Field of Search ............ 426/64, 61, 72, 74, 426/53, 54, 18, 20, 21, 28, 44, 46, 53, 54, 615, 618, 622, 623, 625, 627, 629, 630, 634–636

[56] References Cited

U.S. PATENT DOCUMENTS

| | | | |
|---|---|---|---|
| 3,455,696 | 7/1969 | Ukita et al. | 426/61 |
| 3,585,047 | 6/1971 | Fujinsaki | 99/98 |
| 3,615,721 | 10/1971 | Silberman | 99/199 |
| 3,640,723 | 2/1972 | Uhlig et al. | 99/9 |
| 4,326,036 | 4/1982 | Hayes | 435/161 |
| 4,388,330 | 6/1983 | Wobben et al. | 426/51 |
| 4,388,399 | 7/1982 | Weil et al. | 435/99 |
| 4,639,375 | 1/1987 | Tsai | 426/49 |
| 4,670,268 | 6/1987 | Mahmaud | 426/74 |
| 4,833,128 | 5/1989 | Soloman et al. | 426/74 |
| 4,919,936 | 4/1990 | Iwanami et al. | 426/61 |
| 4,990,343 | 2/1991 | Haarasilta et al. | 426/61 |

FOREIGN PATENT DOCUMENTS

| | | |
|---|---|---|
| 0285098 | 10/1988 | European Pat. Off. . |
| 2302336 | 2/1975 | France . |
| 1212826 | 2/1960 | Germany .............. 426/61 |
| 2602260 | 8/1977 | Germany .............. 426/61 |
| 48-77085 | 1/1972 | Japan . |
| 53-62848 | 6/1978 | Japan . |
| 58-141755 | 8/1983 | Japan . |
| 63-269993 | 11/1988 | Japan . |
| 63-279761 | 11/1988 | Japan . |
| WO85/04201 | 9/1985 | WIPO . |

OTHER PUBLICATIONS

JP 63-209586, beta-mannanose-composition and production thereof, Dec. 23, 1988, abstract only, Patent Abstracts of Japan.
Paul Matsudaira "Sequence from picomole quantities of proteins electroblotted onto polyvinylidene difluorida membranes," J. Biol. Chem. 262:10035–38 (1987), p. 30, line 27.
Feedstuffs 62:10 (1990), p. 2, line 9.
Methods in Enzymology, vol. 160, pp. 180–187 and pp. 368–377.
Methods in Enzymology, vol. 160, pp. 10–19.
Ebisu et al., "Conserved structures of cell wall protein genes etc., " J. Bacteriol. 173(3):1312–1320 (1990), p. 19.
A. Araujo et al., "Hemicellulases of Bacillus species: preliminary comparative studies etc." J. Applied Bacteriol 68:253–261 (1990), p. 13, line 13.

(List continued on next page.)

Primary Examiner—Joseph Golian
Assistant Examiner—Leslie Wong
Attorney, Agent, or Firm—Foley & Lardner

[57] ABSTRACT

Soil microorganisms are obtained that produce a hemicellulase which is particularly useful in increasing the available energy content of hemicellulosic foodstuffs. These microorganisms can be cultured per se or can be used as sources of genetic information with which to engineer other microorganisms to produce the enzyme. Thus, commercially useful quantities of native or recombinant hemicellulase can be produced with cultures consisting essentially of microorganisms that produce the enzyme. The hemicellulase can then be employed in a feed composition containing complex carbohydrates which the enzyme degrades, enhancing the nutritional value of the composition.

10 Claims, 5 Drawing Sheets

OTHER PUBLICATIONS

Almin et al., "Extracellular enzyme system utilized by the Fungus *Sporotrichum pulverulentum* etc." Eur. J. Biochem. 51:207–211 (1975).

Almin and Eriksson, "Enzymic degradation of polymers, II. Viscometric determination of cellulase activity in absolute terms," Biochim. Biophys. Acta 139: 248–253 (1967).

Almin and Eriksson, "Enzymic degradation of polymers, I. Viscometric method for the determination of enzymic activity," Biochim. Biophys. Acta 139:238–47 (1967).

Methods in Enzymology, vol. 160, pp. 522–633.

Hamamoto et al., "Nucleotide sequence of the xylanase A gene of alkalophilic Bacillus sp. strain C-125," Agric. Biol. Chem. 51(3):953–55 (1987).

Esteban et al., "B-D-Xylanases of Bacillus Circulans WL-12," Can. J. Microbiol. 28:733–39 (1982).

Hansen et al., "Alginase enzyme production by *Bacillus circulans*," Appln. Environ. Microbiol. 47(4):704–09 (1984).

Patel et al., "The effect of autoclaving and enzyme supplementation of guar meal on the performance etc." Poultry Sci. 64:1148–1156 (1985).

Al-Ani et al., "Effect of chemical pretreatments on the fermentation and ultimate digestibility etc.", J. Sci. Food Agric. 42:19–28 (1988).

S. V. S. Verma et al., "Guar meal in diets for broiler chickens," British Poultry Sci. 23:95–105 (1982).

Ray et al., "The effect of a purified guar degrading enzyme of chick growth", Poultry Sci. 61:488–494.

Trank et al., "Isolated soy protein production using temperature sensitive gels", Food Technology, Jun. 1989, pp. 78–83.

J. S. Hamada et al, "Prepartion and functional properties of enzymatically deamidated soy proteins", J. Food Sci. 54(3):598–601 (1989).

Teves et al., "Nutritional Value of Copra Meal Treated with Bacterial Mannanase in Broiler Diets", In: Recent Advances in Biotechnology and Applied Biology, Proceedings of Eighth International Conference on Global Impacts of Applied Microbiology and International Conference on Applied Biology and Biotechnology, Aug. 1–5, 1988, Hong Kong, Chinese University Press, pp. 497–507 (1988).

HEMICELLULASE SUPPLEMENT TO IMPROVE THE ENERGY EFFICIENCY OF HEMICELLULOSE-CONTAINING ANIMAL FEED

This application is a continuation of application Ser. No. 07/529,327, filed May 29, 1990, now abandoned.

BACKGROUND OF THE INVENTION

Different enzymes are categorized as a specific type of hemicellulase—a glucanase, a xylanase or a mannanase, for example—based on an ability to catalyze the hydrolysis of heteropolysaccharides composed of glucan, xylan or mannan, respectively. It is known that enzymes that effect hydrolysis of mannans, such as a galactan or a glucomannan, are produced by various microorganisms, including bacteria and fungi, and that they also occur in some animals and in numerous plants. Among the microorganisms that produce such mannanases are species of Aeromonas, Aspergillus, Streptomyces, Rhodococcus and Bacillus. See 160 METHODS IN ENZYMOLOGY Part A, Sect. II (1988).

Hemicellulases have been employed commercially in the processing of coffee, chocolate, cocoa, tea and cereals. The primary advantage gained by using a hemicellulase in this regard is a reduction in solution viscosity which allows for more inexpensive processing of food products. Thus, hemicellulases are used to clarify fruit juices, to reduce the viscosity of slurries or purees, to liquefy certain cell wall solids, and to modify taste. But if the available energy content of human food and animal feed products could be increased, particularly in animal feed, there would be opportunities for cost savings. The successful use of glucanase-treated barley as a corn substitute in avian diets is one such example. See *Feedstuffs* 62: 10 (1990).

Hemicellulosic materials such as alfalfa, coconut residue, guar, locust bean gum, carob bean gum, cassava, copra and soybeans are common constituents of food and feed products. Soybean derivatives comprise a substantial proportion of the ingredients of tofu for human consumption, for example, and soybean protein is used in many feeds for dogs and cats, swine, fish and chickens. Soybean meal may comprise as much as 25% of the feed for baby chickens. The feed rations for chickens, such as broilers, are complex mixtures, formulated from a number of components on a least cost basis. The rations are required in very large volumes. As a result, costly storage facilities for the feed components are necessary for the blending operations. The feed components are blended to provide an optimal nutritional mixture of protein, essential amino acids, minerals, vitamins and calories (that is, an energy source). Soybean meal has been found to be a preferred concentrated source of protein with amino acids and, while not considered a primary energy source such as yellow corn, it supplies about 20% of the energy requirements of broiler chickens.

Although soybean meal provides some carbohydrates and oils which yield energy, approximately 10% of its total carbohydrate content is comprised of galactans and pentosans. These carbohydrates are not absorbed to any appreciable degree by monogastric animals as the animals are unable to digest them rapidly enough to obtain the appropriate monosaccharide for further biochemical oxidation. One approach to increasing the energy content of soybean meal would be to reduce the galactans and pentosans to low molecular weight oligosaccharides or monosaccharides like glucose or similar carbohydrate components which can be more easily metabolized by monogastric animals.

A need therefore exists for a way to increase the available energy content of the hemicellulosic component of food and feedstuffs by converting mannan-containing hemicellulose components therein into lower molecular weight carbohydrates which can be metabolized by monogastric animals.

SUMMARY OF THE INVENTION

It is therefore an object of the present invention to provide a hemicellulase-containing composition that, because it also contains a novel hemicellulase, has an enhanced energy content when consumed.

It is also an object of the present invention to provide a method of producing nutritive materials that contain complex carbohydrates but that nevertheless are usable by a human or monogastric animal.

In accomplishing these and other objects, there has been provided, in accordance with one aspect of the present invention, a consumable composition comprising (A) protein, vitamins and minerals nutritionally suitable for a monogastric animal or a human; (B) a source of carbohydrates, comprising a mannan-containing hemicellulose; and (C) an enzyme that catalyzes the degradation of said mannan-containing hemicellulose, wherein the enzyme has a pH profile for its activity in catalyzing said degradation that ranges from about pH 4.5 to about pH 11. In a preferred embodiment, the consumable composition is for human consumption, i.e., its constituents meet applicable regulatory requirements for human food, as opposed to animal feeds. In another preferred embodiment, by contrast, the composition is for a monogastric animal and, hence, need meet only those requirements which apply to animal feeds.

In accordance with another aspect of the present invention, a composition containing the above-described components described has been provided that includes, as component (C), an enzyme that is active in catalyzing the degradation of mannan-containing hemicellulose under conditions where both (1) pH is in the range of 8–11 and (2) temperature is at least 60° C.

In accordance with still another aspect of the present invention, a consumable composition is provided that comprises soybean meal and an enzyme component that consists essentially of a Bacillus hemicellulase having a pH profile, relative to its activity in catalyzing degradation of hemicellulose, that ranges from about pH 4.5 to about pH 11. In one preferred embodiment, the aforementioned pH profile peaks between about pH 7 and about pH 9.

In accordance with yet another aspect of the present invention, a nutritive method has been provided that comprises the steps of (A) preparing a consumable composition comprised of protein, vitamins and minerals nutritionally suitable for a monogastric animal or human, and further comprising a carbohydrate source comprised of mannan-containing hemicellulose; and (B) incorporating into that composition an enzyme that catalyzes the degradation of the mannan-containing hemicellulose, wherein the enzyme has a pH profile for its activity in catalyzing said degradation that ranges from about pH 4.5 to about pH 11, such that said enzyme renders the mannan-containing portion of said hemicellulose usable by a monogastric animal or a human. In a preferred embodiment, the aforementioned source of carbohydrates is vegetable matter selected from the group consisting of soybeans, alfalfa, guar, locust bean gum, carob bean gum, cassava, copra and coconut residue, and more preferably soybeans and alfalfa. In another preferred embodiment, step (B) comprises producing a mixture containing the enzyme and the composition and then pelletizing that mixture.

Other objects, features and advantages of the present invention will become apparent from the following detailed description. It should be understood, however, that the detailed description and the specific examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

In drawings which illustrate embodiments of the invention.

DETAILED DESCRIPTION OF THE PREFERRED EMBODIMENTS

It has been discovered that a hemicellulase capable of catalyzing the degradation of hemicellulose in a food material, with a resulting increase in available energy content of that material, can be obtained from microorganisms which produce the enzyme. Microorganisms having the ability to produce a hemicellulase within the present invention can be isolated by conventional methods from the soil, where they comprise a reproducible, finite subsection of indigenous microflora. Hemicellulase-producing microorganisms can also be produced by transforming another microorganism, such as *B. subtilis* or *B. brevis*, with hemicellulase-encoding DNA obtained, via standard recombinant DNA techniques, from such indigenous soil microflora.

In cultures consisting essentially of microorganisms that produce a hemicellulase of the present invention, commercially significant quantities of the enzyme can be obtained by isolation techniques well known in the art. In this description, a "culture consisting essentially of a specified type of microorganism," such as a hemicellulase-producing microorganism, is a culture that is comprised primarily of microbes of that type, to the extent that the salient functional property or properties of the culture are determined by those microbes. But other types of microorganisms may be present, for example, in a culture consisting essentially of a hemicellulase-producing microorganism, so long as the other types do not interfere significantly with hemicellulase production by the culture.

Microorganisms which produce a hemicellulase within the present invention can be isolated from soil samples collected from diverse geographical areas. The soil samples are collected primarily from the top two inches of soil and cultured in selective enrichment media.

Techniques for selectively isolating microorganisms with certain desired characteristics are well known in the art. Microorganisms can be selected for the capacity to produce a particular enzyme by exposing samples potentially containing such microorganisms to conditions wherein replication and growth are dependent upon the capacity to produce the desired enzyme. One widely used method of selection is exposing a sample containing a large and diverse population of microorganisms to a medium consisting of a single carbon source. See 160 METHODS IN ENZYMOLOGY 180-86 (1988). Only those microorganisms capable of producing enzymes that can degrade the carbon source will be recovered by this method. Selective culturing techniques of this sort effectively separate microorganisms producing the desired enzyme from the myriad of other microorganisms comprising the normal flora of the habitat sampled.

In a preferred embodiment of the present invention, aliquots of soil samples are inoculated into an alkaline culture medium, wherein hemicellulose serves as the sole carbon source. Dilutions of the sub-cultures grown in the same medium are plated out onto a solid medium which also contains hemicellulose as the sole carbon source. Morphologically distinct colonies are isolated and then screened for hemicellulase activity. In a particularly preferred embodiment of this invention, a selective enrichment broth at a pH range of 99.5, wherein guar is the sole carbon source is inoculated with a sample of soil, incubated at 37° C. and aerobically agitated. After incubation, further dilutions of the initial culture are made using the selective enrichment broth. After several passages, a dilution series of the most dilute broth culture is made in normal saline and plated out on a solid medium which contains guar as the sole carbon source. After incubation at 34° C. for 5-7 days, morphologically distinct colonies are isolated from the solid medium and screened for hemicellulase activity.

The initial selection for microorganisms which utilize hemicellulose as a sole carbon source at an elevated pH results in the recovery of a finite fraction of all soil microorganisms. Typically, about 40% of the isolates are characterized by an ability to produce a hemicellulase of the present invention. A particularly preferred subgroup of this fraction includes species of the Gram-positive genus Bacillus.

Exemplary of this preferred subgroup is a strain of *B. circulans* designated CMG1240, the general properties of which are summarized in Table I below. Strain CMG1240 has been deposited, in accordance with the Budapest Treaty, at the American Type Culture Collection (Rockville, Md.) under accession No. 55045. The key characteristic of strain CMG1240, as for any microbial strain of the preferred subgroup, is its ability to produce in culture medium a hemicellulase suitable for use according to the present invention.

Conventional methods for measuring cellulase/hemicellulase activities are described, for example, in 160 METHODS IN ENZYMOLOGY 180-86 & 368-76 (1988). These methods generally entail exposing a predetermined amount of a substrate to a predetermined amount of a enzyme preparation, crude or purified. The rate of conversion of the substrate to the desired end product is measured under specified conditions of pH and temperature. Crude enzyme preparations can be produced by culturing microorganisms in a suitable medium and then concentrating the enzyme that accumulates in the broth surrounding the cells using conventional means such as precipitation or ultrafiltration. The resulting enzyme preparations can be assayed for specific activity by methods known to the art, including those that are keyed, respectively, to weight loss of insoluble substrates, changes in turbidity of polysaccharide suspensions, an increase in reducing end groups, a decrease in the viscosity of polysaccharides such as β-mannans, colorimetric determinations, measurements of clearance zones in polysaccharide-agar, or polarography.

TABLE I a. Morphology
 (1) bacillus shape; $(0.8 \times 1.7-2.3)\mu m$
 (2) occurs predominately in singles and pairs
 (3) capable of forming endospores
 (4) Gram-positive (also appears Gram-variable or Gram-negative)
b. Growth Conditions
 (1) Tryptic soy agar plate culture: colonies are irregular, convex, smooth, undulate, butyrous, opaque, and 2 mm in diameter (72 hours, 37° C.)
c. Biochemical Properties:
 (1) aerobic
 (2) catalase positive
 (3) oxidase negative
 (4) non-motile
 (5) growth temperature: 30°-50° C., maximum growth rate occurring at 41° C.
 (6) growth pH (cultured at 34° C. at 350 rpm for 10 hours in a basal glucose-mineral salts medium): 7.0-8.5, maximum growth rate occurring at pH 7.5
 (7) casein and gelatin decomposition: negative
 (8) starch hydrolysis: positive
 (9) growth in 1-5% NaCl: positive
 (10) carbon sources utilized include: D-glucose, D-galactose, D-fructose, D-xylose, lactose, maltose, sucrose, α-cyclodextrin, dextrin, glycogen, N-acetylglucosamine, L-arabinose, cellobiose, gentiobiose, lactulose, mannitol, D-mannose, D-melibiose, D-trehalose, turanose, α-ketobutyric acid, uridine, and m-inositol
 (11) hydrogen sulfide production: negative
 (12) indole production: negative
 (13) utilization of citrate: negative
 (14) urease: negative
 (15) Voges-Proskauer: negative
 (16) phenylalanine deaminase: negative
 (17) lysine decarboxylase: negative
 (18) ornithine decarboxylase: negative
 (19) arginine dehydrolase: negative In accordance with the present invention, soil isolates are screened for hemicellulase production by culturing isolated colonies of the microorganisms in a hemicellulose-containing broth medium. After incubation, the broth medium is centrifuged and the resulting supernatant is filtered to remove cells and to produce a crude preparation of hemicellulase. The enzyme is added to alkaline, viscous preparations of a preferred hemicellulose and the degree of liquefaction of the substrate over time is measured.

It is preferred that soil isolates are cultured in a broth medium wherein a mannan-containing hemicellulose is the sole carbon source. After incubation, the broth medium is centrifuged and the resulting supernatant is filtered. The resulting crude enzyme preparation is added to a highly viscous preparation of a mannan-containing hemicellulose at a pH in the range of 8-11. The relative activity of the enzyme is determined by the amount of time required to liquefy the hemicellulose.

It is particularly preferred that soil isolates are cultured, as described above, in a selective enrichment medium wherein guar is the sole carbon source. After incubation, the culture is centrifuged and the resulting supernatant filtered to recover crude enzyme. The crude enzyme is then introduced into tubes containing a cross-linked guar preparation, with metal ions added to enhance the viscosity of the preparation, at a pH in the range of 9-9.5. After incubation for at least one hour at 39°-40° C., enzyme activity is measured by determining the viscosity of a enzyme/guar solution using conventional viscosimetric procedures. See, e.g., Biochim. Biophys. Acta 139: 238 & 248 (1967); Eur. J. Biochem. 51: 207 (1975).

A hemicellulase obtained as described above will generally display an activity characterized by a pH profile—the curve defined by the relationship between a given enzymatic activity and pH—that ranges over some 6.5 pH units, between minima at about pH 4.5 and about pH 11, respectively. Such a pH profile is highly distinctive when compared, for example, to corresponding profiles for known Bacillus mannanases, which are virtually inactive at above about pH 8. See Araujo & Ward, J. App. Bacteriol., 68: 253-61 (1990).

A hemicellulase used in the present invention preferably has a pH profile with a peak (i.e., the portion of the profile where activity is greatest) that is in a range from about pH 9 to about pH 7. It is also preferred that the enzyme display significant biological activity under conditions characterized both by high alkalinity and by elevated temperatures. Such a suitable enzyme would display significant activity, for example, when pH is in the range of 8-11 and the temperature is 60° C. or higher.

A hemicellulase particularly preferred for use according to the present invention is an endo-β-D-mannanase having the following properties:

(1) Activity: A preferred enzyme acts on hemicellulosic materials containing mannan carbohydrates like galactomannan, glucomannan and mannan. Activity in this context can be measured in the following way. An aqueous suspension containing 1.0% guar is used as a substrate, and 2 mL of 2M glycine is added to 16.0 mL of the substrate. The mixture is mixed thoroughly and then preheated to 38° C. Enzyme is added to the substrate, mixed well and then the viscosity of the enzyme/guar solution is measured using a simple approach, as by timing the charging and discharging of a pipette with stopwatch, or more complex devices like Brookfield or Fann viscometers. A standard curve is prepared using a commercially available hemicellulase enzyme with known activity such as Miles B1500.

Grams or units of the commercially available hemicellulase are plotted against the time required to change viscosity and the new hemicellulase is compared to that of the commercial product.

(2) Substrate specificity: The enzyme degrades relatively simple carbohydrate polymers like guar gum, which is a polymer of D-mannose linked $\beta$-1,4 with D-galactose, and locust bean gum, as well as more complex, mannan-containing carbohydrates, for example, from soybean and alfalfa. Other suitable substrates will include mannan-containing coconut residue, carob bean gum, cassava, copra, and chemically-modified forms of guar.

Figure 2:
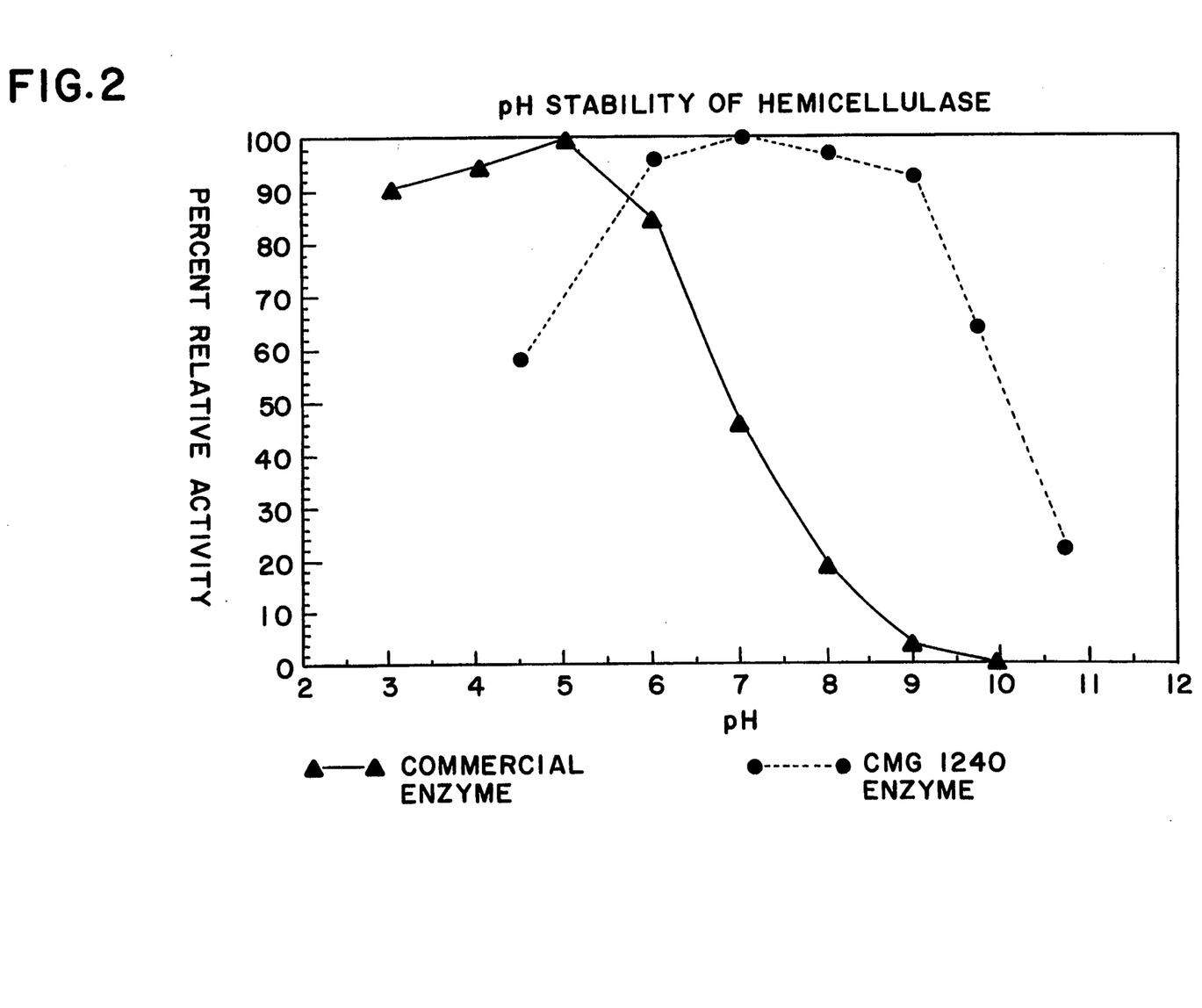
FIG. 2 is a graph that compares the pH profile of enzymatic activity for a hemicellulase of the present invention versus a known, commercially available enzyme.

(3) Optimum pH: The optimum pH of the enzyme is about 7.0 or slightly above, e.g., in the range 7.1 to 7.5. The enzyme is stable in a pH range of about 4.5 to 11 (see FIG. 2).

Figure 1:
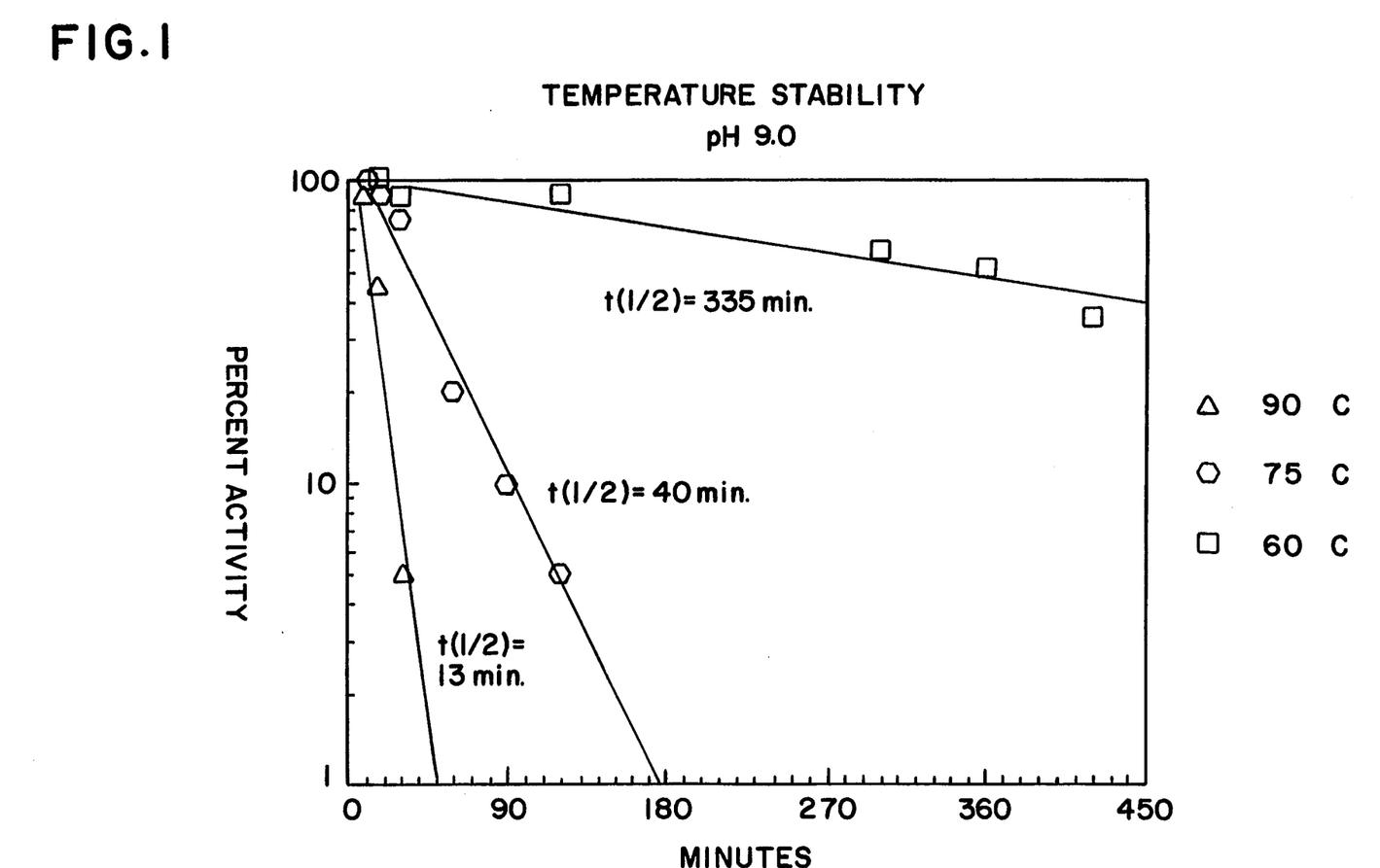
FIG. 1 is a graph which plots the activity of a hemicellulase within the present invention versus time (pH 9.0) at 60°, 75° and 90° C., respectively.

(4) Optimum temperature: The optimum temperature for enzyme activity is 40° C., but enzyme activity is observed at temperatures ranging from 20° to 90° C. As shown in FIG. 1, the enzyme exhibits significant activity at temperatures ranging from 60° C. to 90° C.

(5) Deactivation by Temperature and pH: At pH 9.0 the enzyme retains 50% of its maximum activity after 5.5 hours at 60° C., after 45 minutes at 75° C., and after 15 minutes at 90° C. (see FIG. 1).

(6) Molecular Weight: After purification to homogeneity, the enzyme has a molecular weight of about 32,000 as determined by SDS-polyacrylamide gel electrophoresis. To obtain a crude enzyme preparation from culture broth, cells and debris are first removed with a 0.1-micron filter. The enzyme is then concentrated with a 10,000 molecular weight cut-off membrane. However, once the enzyme becomes quite concentrated, a good proportion of the enzyme is able to pass through the membrane. The enzyme in this final permeate can be concentrated with a 5,000 molecular weight cut-off membrane or precipitated with three volumes of acetone. After the precipitate is centrifuged, the supernatant is siphoned off and the pellet resuspended in 50 mM phosphate buffer. This concentrate is dialyzed versus 10 mM phosphate buffer (pH 7.0) and then applied to a DEAE-Sephacel column. The enzyme is eluted with a solution gradient of sodium chloride of increasing ionic strength ranging from 0–1.25M in 50 mM phosphate buffer (pH 7.0). Fractions are collected and tested for enzyme activity. The fractions exhibiting maximum activity are pooled and examined using SDS-polyacrylamide gel electrophoresis and compared to protein molecular weight standards.

Pursuant to the present invention, commercially useful quantities of hemicellulase can be produced by culturing the foregoing hemicellulase-producing microorganisms using conventional fermentation techniques. In this context, "fermentation" is used broadly to refer to any controlled microbial action by which useful products are obtained from the substrate(s) of that action. In accordance with the present invention, fermentation can be carried out in a stirred-tank reactor. This type of reactor is essentially a closed cylindrical tank containing agitators, baffles, heat exchange coils, and automatic controls for temperature, air flow, pressure, pH and foaming. A fermenter of this sort would be charged with essential nutrients and a hemicellulase inducer. After sterilization, the reactor is inoculated with a culture consisting essentially of microorganisms that have been selected for their capacity to produce hemicellulase as described above.

Continuous culture can increase fermenter productivity by eliminating the downtime of batch cultures. But it is sometimes difficult to maintain sterility in large scale continuous cultures. Accordingly, batch fermentations which utilize the bacteria of the present invention are preferred.

In a preferred embodiment of this invention, a Gram-positive Bacillus strain, such as B. circulans CMG1240, is utilized to produce commercially useful quantities of the enzyme. A fermenter charged with a medium consisting of industrial-grade nutrients, glycerol (carbon source) and a mannan-containing hemicellulose, such as guar gum, is inoculated with a culture consisting essentially of a Gram-positive Bacillus strain as described above. The fermenter is maintained at about 35° C. (500–1,000 rpm agitation) for about 12 hours. The hemicellulose, such as guar, is added to the fermenter during the growth phase to further induce enzyme production. The fermentation is harvested after about 1 to 7.5 hours, and then enzyme activity is measured, for example, by viscometric means.

Enzyme activity of the fermentation product is assayed by centrifuging aliquots of the fermentation broth and testing the resultant supernatant. Aliquots of the supernatant (or dilutions thereof) are added to a guar solution and any reduction in the viscosity of the enzyme/guar solution is measured routinely by recording the time required for a constant bore pipette to discharge a predetermined volume [see item (1) under the preferred hemicellulase properties discussed above].

The enzyme is recovered from the fermentation broth by filtration through a 0.5-micron filter to remove cells followed by ultrafiltration using a 5,000 or 10,000 molecular weight cut-off ultrafiltration membrane. The concentrate is combined with three volumes of acetone at about 4° C. to precipitate the enzyme. The precipitate is allowed to settle for approximately 24 hours before the supernatant is siphoned off. The precipitate is then centrifuged at about 4° C. and the resultant pellet resuspended in phosphate buffer to form a paste.

In an alternative method for producing a hemicellulase within the present invention, DNA encoding hemicellulase could be isolated and used, via known procedures, to transform a suitable host organism such that the enzyme is produced by the recombinant host in commercially useful amounts. Hemicellulase-encoding DNA could be isolated by screening nucleic acid libraries generated from microorganisms expressing a hemicellulase according to the present invention. See, e.g., Ausubel et al., CURRENT PROTOCOLS IN MOLECULAR BIOLOGY at §§5 and 6, John Wiley and Sons, New York (1987, 1990) ("Ausubel"). Such libraries would be screened by means of oligonucleotide probes that are complementary to a polynucleotide encoding, for example, a portion of the N-terminus of a hemicellulase within the present invention. Illustrative of such an N-terminal portion is the amino acid sequence Ala-Ser-Gly-Phe-Tyr-Val-Xxx-Gly-Thr-Ile-Leu-Xxx-Asp-Ser-Thr-Gly-Asn-Pro-Phe-Lys-Ile-Xxx-Gly-Xxx-Asn [Xxx denotes an indeterminant amino acid], as discussed in Example 12 infra. See Ausubel at §6.

Alternatively, other portions including or adjacent to the endogenous coding sequence of a hemicellulase according to the present invention can be used, when isolated using a probe as a template for generating other probes useful for isolating a hemicellulase-encoding polynucleotide according to the present invention, e.g., based on the N-terminal sequence described above. Such a probe could be used in a known manner to screen a genomic or cDNA library as described above, see Ausubel, loc. cit., or to synthesize polymerase chain reaction (PCR) probes for use in amplifying a cDNA generated from an isolated RNA which codes for a hemicellulase of the present invention. Such a cDNA could then be cloned into a suitable expression vector and employed to transform a host organism. See Ausubel at §15.4.

A suitable polynucleotide in this regard would preferably comprise a nucleotide sequence, corresponding to the desired amino-acid sequence, that is optimized for the host of choice, as described below, with regard to codon usage, the initiation of translation, and the expression of recoverable amounts of a commercially useful hemicellulase within the present invention. Also, a vector selected for transforming the chosen host organism with such a polynucleotide molecule should allow for efficient maintenance and transcription of the sequence encoding the polypeptide. Such a vector is readily available or derivable from commercial sources, and is suited to a particular host cell employed for expressing a hemicellulase according to the present invention. For vectors exemplary of those suitably used to the present invention, see Ausubel at §§2–4.

Host cells suitable for expressing a hemicellulase according to the present invention would include prokaryotic or eukaryotic cells, for example, bacterial, algal, yeast, insect, mammalian and human cells. Thus, among host cells suitable for the present invention would be microorganisms of the genera Aeromonas, Aspergillus, Bacillus, Escherichia, Kluyveromyces, Pichia, Rhodococcus, Saccharomyces and Streptomyces. More specifically illustrative of the suitable host microorganisms would be the bacteria *E. coli, B. subtilis, B. brevis* (J. Bacteriol. 172: 1312–20) and *B. circulans,* as well as the yeast *S. cerevisiae* strain X2181-1B, with genotype a trp1 gal1 ade1 his2 (available from the Yeast Genetic Stock Center, Berkeley, Calif.); strain ATCC 52683, with genotype ade1 trp1 met14 ura3 (available from the American Type Culture Collection, Rockville, Md.); and strain ATCC 46183, with genotype a his1 trp1 (also available from the American Type Culture Collection). Host cells comprising a polynucleotide encoding a hemicellulase according to the present invention can be grown under conditions that provide expression of a hemicellulase of the present invention in recoverable or commercially useful amounts. See, e.g., Ausubel at §§1 & 13.

Many sources of vegetable matter such as soybeans are rich in energy containing proteins and carbohydrates and are frequently utilized as a component of animal feed. Soybeans are also widely used as components of food products for human consumption. Galactans are a major component of the total carbohydrate content of commercial soybean products, however, and do not contribute significantly to the available energy content of soybean meal when employed as a component of feed for monogastric animals because these carbohydrates are not easily digested, and consequently, they are not absorbed. In order to exploit their energy content, galactans must be reduced to smaller molecular weight carbohydrates which can be absorbed and metabolized by monogastric animals and humans.

In accordance with the present invention, a hemicellulase possessing the above-mentioned properties can be employed to degrade galactans and other mannan carbohydrates present in hemicellulosic constituents of food and animal feedstuffs, especially those containing complex carbohydrates from soybeans. It is preferable that the enzyme component included in a consumable composition of present invention should consist essentially of a hemicellulase, particularly a *Bacillus hemicellulase,* as described above. In this regard, "consisting essentially" means that the enzyme component displays a hemicellulose-degrading activity which is determined principally by the aforementioned hemicellulase. Other enzymes, possibly with other activities, may be present, however, so long as they do not unduly interfere with the hemicellulose-degrading activity of the enzyme component.

In a preferred embodiment, an effective amount of hemicellulase according to the present invention is added to an aliquot of soybean meal and allowed to dry. The resulting composition is ground to a fine powder and then mixed with dry animal feed consisting, for example, of corn and other nutrients.

A mixture of this sort can be processed under conditions, particularly of heat and pH, that would inactivate conventional hemicellulases. Thus, the aforementioned soybean-based composition can be processed through a press mill to form pellets of animal feed containing hemicellulase, soybean meal and other animal feed components in predetermined proportions. When maintained on a diet of the hemicellulase-containing animal feed, chickens on the average gain more body weight per pound of feed ingested than chickens maintained on an identical diet absent hemicellulase.

The present invention is further described below by reference to the following illustrative examples. In those examples, the following media were employed:

| Selective Enrichment Broth (amount/liter) | |
|---|---|
| 10.0 g | Guar Gum |
| 5.0 g | $(NH_4)_2SO_4$ |
| | pH 9.5 |
| Selective Enrichment Agar (amount/liter) | |
| 2.0 g | Guar Gum |
| 1.0 g | $Na_2HPO_4$ |
| 3.0 g | $(NH_4)_2SO_4$ |
| 0.2 g | NaCl |
| 0.2 g | $MgSO_4.7H_2O$ |
| 50.0 mg | $CaCl_2.2H_2O$ |
| 1.0 mL | Trace Elements Solution I (see below) |
| 15.0 g | Agar Noble |
| 50.0 mM | Tris Buffer (pH 9.0) |
| 1.0 mL | Vitamin Solution (see below) |
| Trace Elements Solution I (amount/liter) | |
| 100.0 mg | EDTA |
| 230.0 mg | $ZNSO_4.7H_2O$ |
| 180.0 mg | $MnSO_4.H_2O$ |
| 60.0 mg | $H_3BO_3$ |
| 100.0 mg | $CuSO_4.5H_2O$ |
| 40.0 mg | $Na_2MoO_4.2H_2O$ |
| 40.0 mg | $CoCl_2.6H_2O$ |
| 70.0 mg | KI |
| 40.0 mg | $FeSO_4.7H_2O$ |
| 0.4 mg | $NiCl.6H_2O$ |
| 8.0 µL | 0.1M $H_2SO_4$ |
| Vitamin Solution I (amount/liter) | |
| 1.0 g | Vitamin B12 |
| 1.0 g | Riboflavin, B2 |
| 1.0 g | Pyridoxine, B6 |
| 1.0 g | D-biotin |
| 1.0 g | Thiamine Hydrochloride |
| 1.0 g | Nicotinic Acid |
| 1.0 g | D-Ca-Pantothenic acid |
| Seed Broth (amount/liter) | |
| 7.5 g | Glycerol |
| 10.0 g | Yeast Extract |

| | -continued |
|---|---|
| 2.5 g | Corn Steep Liquor |
| 1.0 g | KH$_2$PO$_4$ |
| 2.0 g | (NH$_4$)$_2$SO$_4$ |
| 0.5 g | MgSO$_4$.7H$_2$O |
| 1.0 mL | Trace Elements Solution II (see below) pH 7.0–7.5 |
| Fermentation Broth (amount/liter) | |
| 20.0 g | Glycerol |
| 20.0 g | Yeast Extract |
| 5.0 g | Corn Steep Liquor |
| 2.0 g | KH$_2$PO$_4$ |
| 4.0 g | (NH$_4$)SO$_4$ |
| 1.0 g | MgSO$_4$.7H$_2$O |
| 2.0 mL | Trace Elements Solution II pH 8.5 |
| Trace Elements Solution II (amount/liter) | |
| 20.0 g | FeSO$_4$.7H$_2$O |
| 20.0 g | FeCl$_3$.6H$_2$O |
| 0.5 g | MnSO$_4$.H$_2$O |
| 50.0 mg | CoSO$_4$.7H$_2$O |
| 10.0 mg | CuSO$_4$.5H$_2$O |
| 20.0 g | CaCl$_2$.2H$_2$O |
| 50.0 mg | H$_3$Bo$_3$ |
| 100.0 mg | ZnSO$_4$7H$_2$O |
| 100.0 mg | Na$_2$MoO$_4$.2H$_2$O |

EXAMPLE 1

Isolation of Hemicellulase-Producing Microorganisms from Soil

Soil samples collected from both a tropical rain-forest and a temperate garden were added to selective enrichment broth in a 10% w/v concentration. The cultures were shaken in baffled Erlenmeyer shake flasks at 37° C. for four days. Four dilutions [1:10, 1:20, 1:800 and 1:50,000] of the initial cultures were made with fresh selective enrichment broth and incubated at 37° C. for four days. The 1:50,000 dilution was used to prepare a dilution series ($10^{-1}$ to $10^{-8}$) in 0.85% NaCl which were plated out on selective enrichment agar and incubated at 34° C. for 5–7 days. Following incubation, isolated colonies were selected from the plated cultures and streaked for purity three successive times on a suitable agar medium. Nine isolates from soil collected from a tropical rain-forest and 24 isolates from soil collected from a temperate garden were selected as a result of this screening process.

EXAMPLE 2

Screening of Soil Isolates for Hemicellulase Activity

Each purified isolate from the tropical rain-forest soil was transferred to a shake flask containing selective enrichment broth and shaken for 48–72 hours at 34° C. After incubation, the culture was centrifuged for 20–30 minutes at 10,000 rpm (4° C.). The resultant supernatant was filtered sequentially through a 0.8- and a 0.45-micron filter to recover crude enzyme free of microbial cells. Each purified isolate from the temperate garden soil was transferred to tubes containing selective enrichment broth and shaken 12–48 hours at 34° C. After incubation, the cultures were centrifuged and filtered as described above. The crude enzyme solution was added to tubes containing 5 mL of a cross-linked guar preparation (5.0 g guar, 2.0 g (NH$_4$)$_2$SO$_4$ and 0.6 g sodium tetraborate per 400 mL water, pH 9.5) and incubated for at least 1 hour in a water bath at 39°–40° C. To measure enzyme activity, a constant bore 1 mL pipette was charged with 1.0 mL of the mixture and allowed to discharge 0.9 mL. A stopwatch was used to measure the time required for this discharge to occur (hereinafter "drop time"). A drop time of less than two seconds indicated measurable amounts of hemicellulase activity. Twelve of the twenty-four isolates recovered from temperate garden soil, and four of the nine isolates recovered from tropical rain-forest soil produced measurable amounts of hemicellulase.

EXAMPLE 3

Production of Commercially Useful Quantities of Hemicellulase

Figure 3:
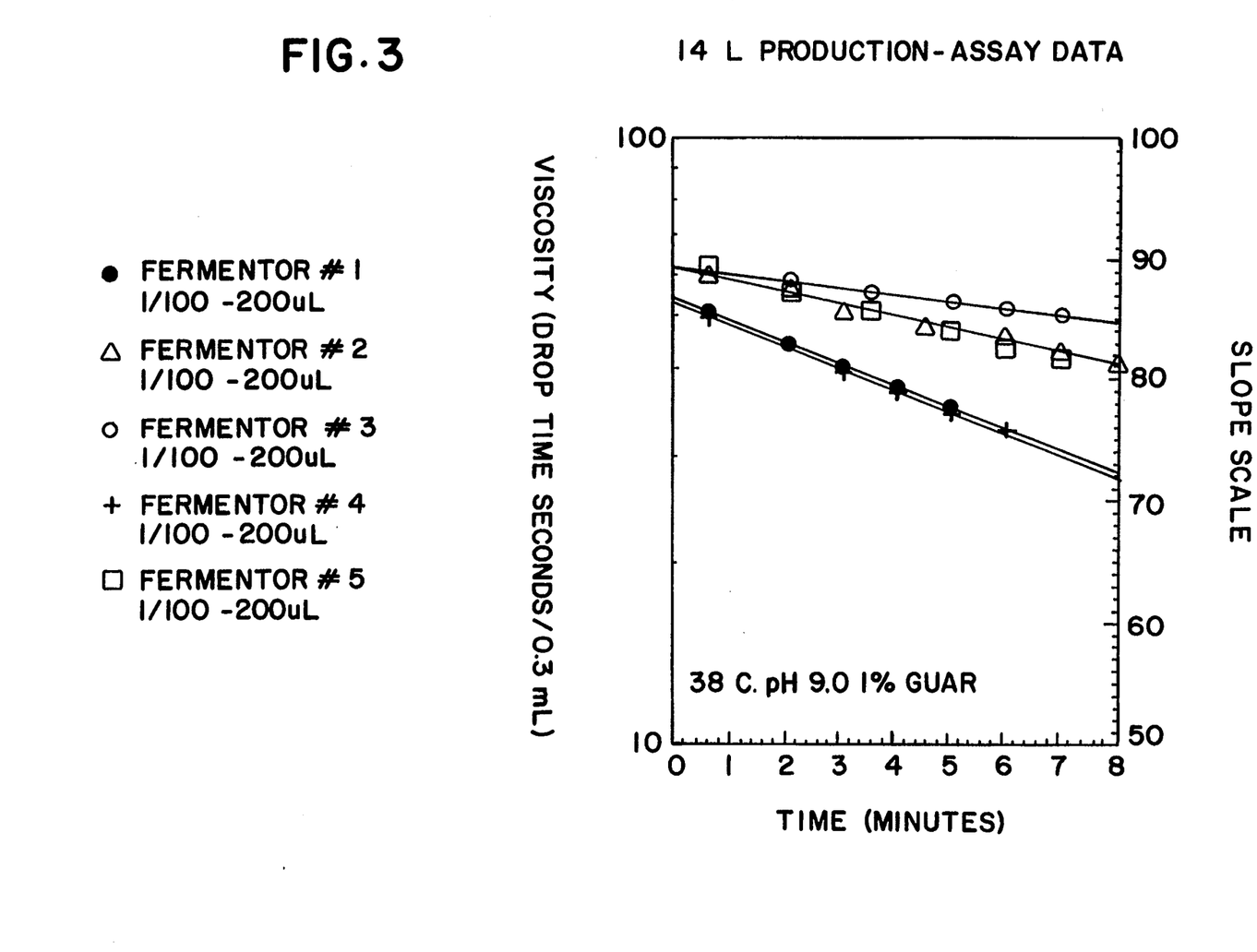
FIG. 3 presents representative data showing the reduction in viscosity in relation to the amount of time the diluted enzyme was incubated with the guar solution.
Figure 4:
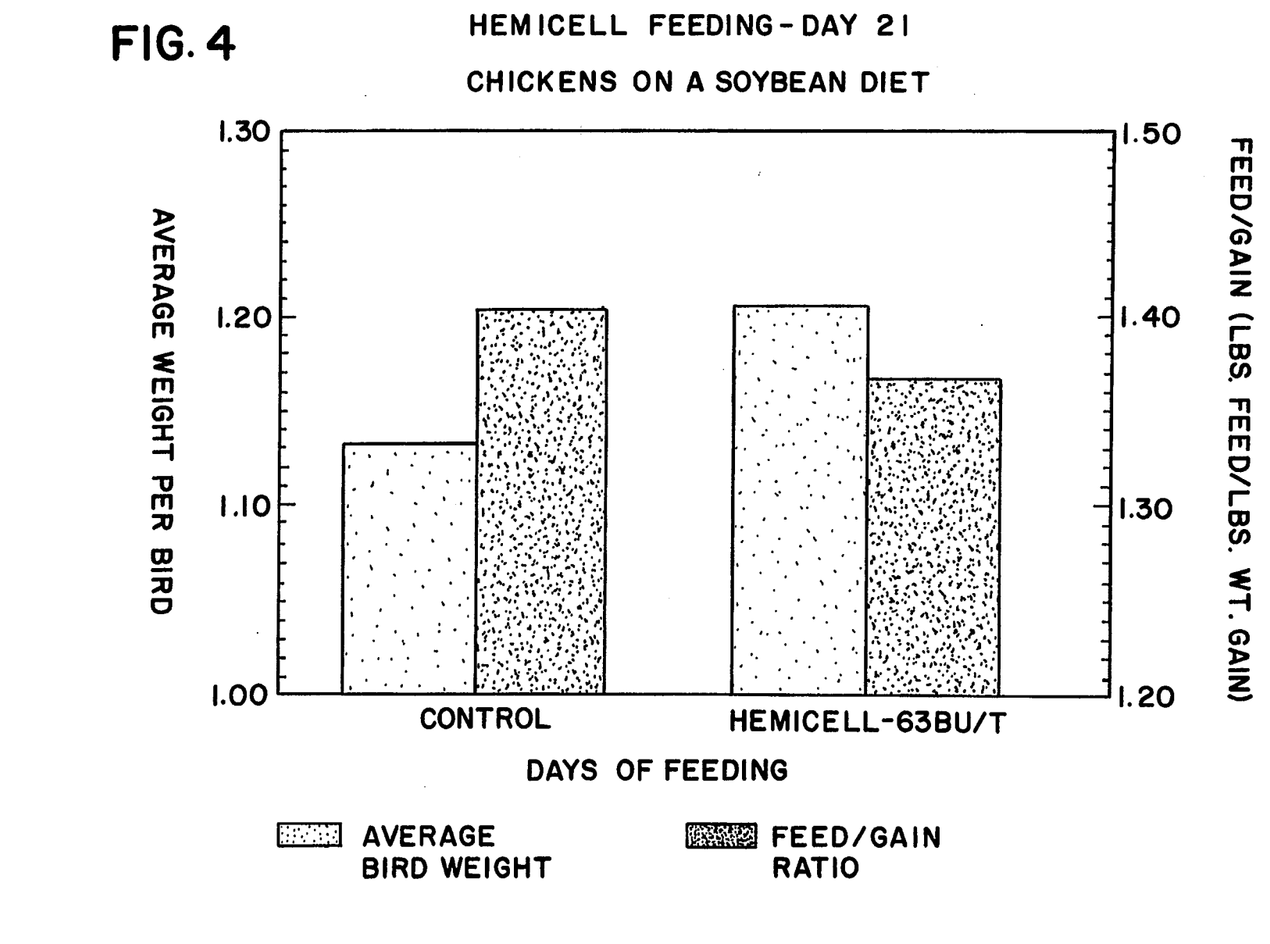
FIG. 4 presents data showing the average weight of chickens maintained for the first 21 days of life on a control diet versus the average weight of chickens maintained on a diet of hemicellulase-containing animal feed. The ratio of the amount of feed consumed to the amount of weight gained (feed/gain) for both populations is also presented.

A single, isolated colony of *Bacillus circulans* (CMG1240) was inoculated into a 500 mL Erlenmeyer baffled shake (pre-seed) flask containing 50 mL of brain heart infusion broth. The inoculated flask was shaken (300 rpm) while incubating for 12–16 hours at 35° C. After incubation, the entire volume of the pre-seed flask was aseptically transferred to a 4 L Erlenmeyer baffled shake-flask (seed) containing one liter of seed medium. The seed-flask was incubated with shaking for 12–16 hours at 35° C. The entire volume of the seed flask was aseptically transferred to a 14-liter fermenter containing 9.0 liters of fermentation broth. The fermenter was maintained at 40° C., >20% dissolved oxygen and 500–1000 rpm. Guar gum was added to make a final concentration of 0.05% to the fermenter two or three times during the growth phase and once (0.5%) during the stationary phase to induce enzyme production. After 1–7.5 hours, the fermentation was terminated and enzyme activity assayed according to the procedure of Example 5. Assay data are shown in FIG. 3.

EXAMPLE 4

Measurement of Hemicellulase Activity to Determine Optimal Culture Conditions for Hemicellulase Production Twenty milliliter aliquots of 1% guar in water, mixed for 3 hours to obtain the maximum viscosity, and 2 mL aliquots of 2M glycine-NaOH buffer (pH 9.0) were added to a glass-jacketed reactor maintained at 40° C. by means of a circulating water bath. Aliquots of the fermentation product were centrifuged in a Microfuge for 5 minutes and the resultant supernatant was used to test for enzyme activity. A 100–200 μL sample of the supernatant was added to the reactor. Enzyme activity was measured as described in Example 5. Sample enzyme activity was calculated from a standard curve prepared by plotting the log of the drop time (seconds) of dilution of a standard hemicellulase (Miles B-1500) versus incubation time in minutes. The slope (on a linear scale) of the log plot was calculated and replotted versus grams or "chamber units" of hemicellulase.

EXAMPLE 5

Assay for Hemicellulase Activity Suitable for Testing Standards and Purified Enzyme Preparations In a procedure suitable for screening enzyme activity of standard hemicellulase or purified enzyme preparations, approximately 16.0 mL of a guar preparation, comprising 1% guar gum in water, and 2.0 mL of 2M glycine (adjusted to pH 9.0 with NaOH), were added to a 100 mL glass jacketed reactor maintained at 38° C. by means of a circulating water bath. The solution was mixed thoroughly by a magnetic stirrer after reaching temperature. Viscosity at time zero was determined by measuring the time required for the solution to drop from the 1.0 mL mark to the 0.7 mL mark in a constant bore, 1 mL pipette. The initial drop time of the guar solution without enzyme added was 75 to 90 seconds. After enzyme addition (200–500 μL) to the reactor, the guar/enzyme solution was allowed to incubate. A time-zero measurement of the solution was immediately determined. Drop time measurements were performed until either five measurements had been made or until the drop time was less than 30 seconds. A standard curve was prepared by plotting the log of the drop time versus the time of incubation using different standard enzyme dilutions.

EXAMPLE 6

Recovery of Hemicellulase from Fermentation

The procedure described in Example 3 was used in the production of useful quantities of hemicellulase in each of six 14-liter fermentations. After the fermentation was terminated, cells were removed from 60 L of culture broth by ultrafiltration with a 0.1-micron filter. Then, the enzyme was concentrated to a volume of approximately 3.5 L with a 10,000 molecular weight cut-off ultrafiltration membrane. The concentrate was combined with three volumes of acetone at 4° C. to precipitate the hemicellulase. The precipitate was collected by allowing it to settle for 24 hours and then siphoning off the supernatant. The precipitate was then centrifuged at 6000 rpm for 10 minutes at 4° C. The resulting pellet was immediately resuspended in 170 mL of 50 mM potassium phosphate buffer (pH 7.0) to a final volume of 300 mL. The enzyme activity of the resulting hemicellulase paste was determined according to the method of Example 5. The recovered hemicellulase paste had $9.45 \times 10^6$ chamber units/liter, which was equivalent to 6.3 kg/L of standard commercial hemicellulase (assayed at pH 9.0) or 1.89 kg total of standard hemicellulase formulation.

EXAMPLE 7

Alternate Process for Recovering Hemicellulase

Hemicellulase was recovered by the method described in Example 6, wherein methanol was used alternatively to precipitate hemicellulase. The supernatant was siphoned off and the precipitate centrifuged as described above. The paste-like precipitate was then blended with 10 volumes (w/w) of lactose and dried under vacuum at temperatures up to 40° C.

EXAMPLE 8

Alternate Process for Recovering Hemicellulase

Hemicellulase was concentrated to a volume of approximately 15 L with a 10,000 molecular weight cut-off ultrafiltration membrane. Solid ammonium sulfate was slowly added to 75% saturation with continuous mixing. The precipitate formed in the resulting solution was harvested by centrifugation at 8,000 rpm for 45 minutes. The enzyme activity of the resulting pellet was determined according to the method of Example 5. The recovery yield of enzyme activity was $1.85 \times 10^5$ units/gram ($2.22 \times 10^8$ total units). The recovery yield of enzyme activity of the precipitate was 77% of the total enzyme activity of the 15 L concentrate.

EXAMPLE 9

Purification of Hemicellulase

To produce a more purified product, two precipitation steps were used to obtain refined enzyme. A concentrate from ultrafiltration was prepared according to the method described in Example 6. The concentrate contained $6.39 \times 10^6$ units/liter, with a specific activity of $1.11 \times 10^3$ units/mg. Equal volumes (2.2 liters) of the concentrate and acetone were mixed to make a 50% (v/v) solution, and the resultant precipitate was then allowed to settle for 18 hours at 10° C. After the supernatant was collected, an additional volume of acetone was added to make the solution 75% (v/v). The resultant precipitate was allowed to settle for 24 hours at 10° C., after which the supernatant was first removed by siphoning and finally by centrifugation at 5000 rpm. The precipitate was then dissolved in 222 mL of 50 mM phosphate buffer (pH 7.0). Activity was determined to be $5.71 \times 10^7$ units/liter, with a specific activity of $6.17 \times 10^3$ units/mg. This purification step resulted in a recovery of 90% of the total activity with only 20% of the protein, causing a 5.56 fold increase in the specific activity.

EXAMPLE 10

Alternative Hemicellulase Purification Process

An alternative purification process was employed to avoid the precipitation step of Example 9. The hemicellulase was concentrated to the desired concentration by ultrafiltration as described in Example 9. A liquid formulation of the concentrate was then prepared by adding stabilizing and preservative agents such as ethylene glycol, or alternatively, glycerol, methanol, ethanol, sorbitol, sodium benzoate, sodium citrate, methylparaben, sodium ascorbate or an equivalent.

EXAMPLE 11

Characterization of the Purified Hemicellulase

A broth concentrate was prepared by ultrafiltration; i.e., cells were removed with a 0.1-micron membrane and the enzyme concentrated with a 10,000 molecular weight cut-off membrane. When the enzyme became concentrated, it was observed that some of the hemicellulase passed through the membrane. This permeate fraction was reconcentrated with the 10,000 molecular weight cut-off membrane and then used for further purification. The reconcentrated permeate was precipitated by the addition of 3 volumes of acetone at 4° C. The supernatant was siphoned off, and the precipitate resuspended in 50 mM phosphate buffer (pH 7.0) to a final volume of 222 mL. The enzyme concentrate was subsequently dialyzed versus 10 mM phosphate buffer (pH 7.0) to remove any salts. The dialyzed concentrate was then applied to a DEAE-Sephacel column ($2.8 \times 30$ cm). Elution of the hemicellulase was carried out by adding a solution of increasing ionic strength to the column at a flow rate of 1 mL/minute. The solution consisted of 0–1.25M NaCl in 50 mM phosphate buffer. Ten milliliter fractions were collected and tested for enzyme activity by measuring viscosity reduction of a 1% guar solution as described in Example 5. Fractions 96–109, which showed maximum activity, were pooled and then analyzed (along with molecular weight marker-proteins) on a 12.5% SDS-polyacrylamide gel. The results of this analysis indicated that the hemicellulase was highly purified, and had a molecular weight of 32,000. Hemicellulase fractions were ultimately purified by electrophoresis on the same type of SDS-gel and blotted onto Immobilon P PVDF membrane and stained with coomassie blue by the method of Matsudaira, J. Biol. Chem. 262: 10035–38 (1987). The hemicellulase band on the membrane was excised and used for amino acid sequence analysis. The enzyme was analyzed by Edman degradation using a Biosystems Gas Phase Sequenator. The N-terminal sequence of the purified enzyme was characterized as follows:

```
1                   5                      10
Ala—Ser—Gly—Phe—Tyr—Val—Xxx—Gly—Thr—Ile—Leu—Xxx—
         15                  20                      25
Asp—Ser—Thr—Gly—Asn—Pro—Phe—Lys—Ile—Xxx—Gly—Xxx—Asn
```

EXAMPLE 12

Composition of Animal Feed to Study Body Weight Gain/Pound Feed Ingested

Three different batches of animal feed were prepared. These batches were referred to as (i) starter feed, (ii) grower feed, and (iii) finisher feed. The compositions of the three batches of feed are presented in Table II.

TABLE II

| INGREDIENT | % STARTER | % GROWER | % FINISHER |
|---|---|---|---|
| Corn yellow | 56.429 | 62.115 | 62.017 |
| Soybean ML-48% protein | 35.429 | 29.619 | 29.745 |
| Corn gluten ML-61% protein | 0 | 0.467 | 0 |
| Fat (3700 kcal/lb) | 4.926 | 4.455 | 4.941 |
| Methionine 88% | 0.243 | 0.304 | 0.318 |
| NaCl | 0.321 | 0.278 | 0.289 |
| Calcium Carbonate | 0.678 | 0.680 | 0.692 |
| Defluorinated Phosphorus* | 1.684 | 1.567 | 1.458 |
| Choline Cl-70% active | 0.090 | 0.105 | 0.105 |
| Trace Mineral Premix | 0.050 | 0.050 | 0.025 |
| Bacitracin MD | 0.050 | 0.050 | 0.050 |
| Vitamin Premix** | 0.050 | 0.050 | 0.050 |
| Coccidiostat*** | — | 0.050 | 0 |
| Liquid marigold extract | 0 | 0.202 | 0.310 |

*32% calcium - 18% phosphorus
**16 common vitamins and essential nutrients
***AgriBio Corporation (Athens, Georgia)

EXAMPLE 13

Preparation of Hemicellulase/Soybean Meal Feed Supplement

The procedure described in Example 3 was used in the production of useful quantities of hemicellulase. The hemicellulase was recovered as described in Example 8. Approximately 2.2 lbs of the resulting hemicellulase paste was mixed with a small aliquot (8.8 lbs) of soybean meal (48% protein) to achieve a concentration of $31.75 \times 10^6$ units of enzyme activity per pound of hemicellulase/soybean meal mixture. The mixture was allowed to air dry in a large open pan under a fume hood. The dried mixture was ground to a fine powder in a Waring blender and stored at 4° C. until used.

EXAMPLE 14

Preparation of Hemicellulase Containing Animal Feed

Three types of animal feed containing 2 lbs of the hemicellulase/soybean meal mixture per ton of feed were prepared. Two pounds of the hemicellulase/soybean meal mixture prepared according to the method described in Example 12 were added to the ingredients (excluding the yellow corn and soybean meal) comprising each of the three types of animal feed prepared according to Example 12. The hemicellulase/soybean meal mixture and the other ingredients were mixed for one minute in a vertical agitator. This mixture was then combined with predetermined amounts yellow corn and soybean meal and mixed in the vertical agitator for 3.5 minutes. The resulting hemicellulase/feed mixture was formed into pellets by processing the feed mixture in a California press mill equipped to deliver moist steam (10% v/w). The feed mixture was stamped into pellets which were cooled immediately in a vertical forced-air cooling tower. The pellets were shaken to remove any fine powder material, which was recycled to the pelleting chamber. The starter feed pellets were crumbled by processing them through a roller mill.

EXAMPLE 15

The Use of Hemicellulase as a Feed Additive

The effect of adding hemicellulase to animal feed containing soybean meal as a factor of the average body weight gain of chickens/pound of feed ingested was studied. One day old chicks (Peterson X Arbor Acres strain) were selected for the study. The birds were vaccinated against Marek's Disease and Newcastle-Bronchitis. Twenty-five birds of each sex were caught at random and weighed to establish an acceptable weight range. A range of $+/-5$ grams of the mean was determined for each sex. Birds were caught at random, screened for proper weight and randomly assigned to a group consisting of 76 mixed sex broiler chicks (38 males and 38 females). In total, there were 7 groups of test and 7 groups of control chickens.

Each group was housed in a separate pen. The temperature of the pens was checked daily for the first two weeks of the study. The house temperature and humidity was checked daily for the duration of the study. Air exchange was enhanced by wall fans. The birds were placed on built-up litter. Wet litter from previous studies was removed and replaced by one inch of new litter. Artificial lighting was provided continuously and all birds had ready access to water.

All birds that died within the first 7 days of the study were replaced with a bird of the same sex from the same shipment of birds. No bird was replaced after 12:01 pm of Day 7 of the study.

Figure 5:
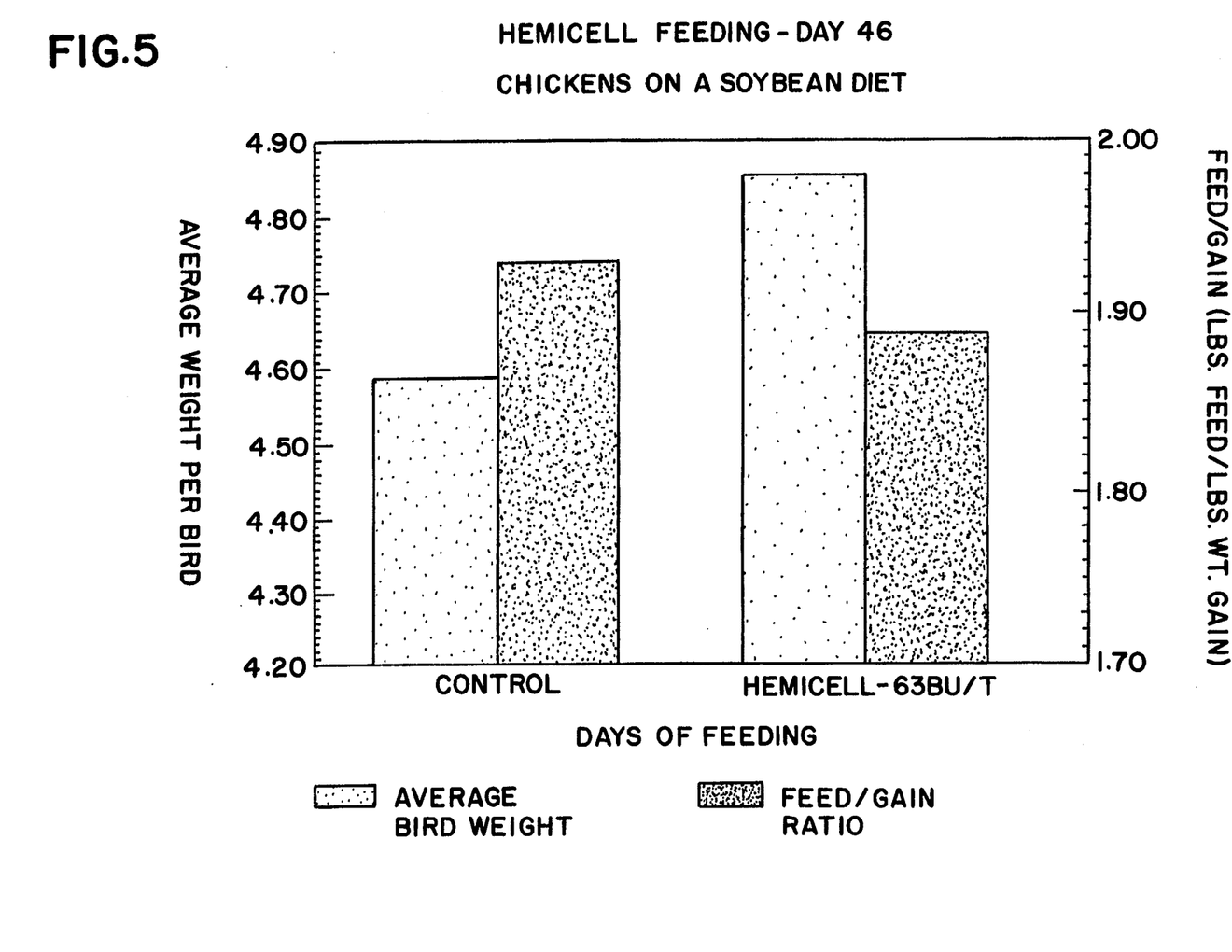
FIG. 5 presents data showing the average weight of chickens maintained for 46 days of life on a control diet versus the average weight of chickens maintained on a diet of hemicellulase-containing animal feed. The ratio of the amount of feed consumed to the amount of weight gained (feed/gain) for both populations is also presented.

All chicks were placed on their respective diets on Day 0 of the study. The chicks were fed crumbled pellets of starter feed on Days 0–21. On Days 22–39, the chicks were fed pellets of grower feed. On Days 40–46, the chicks were fed pellets of finisher feed. The pens were checked three times daily during the study. Birds that died during the study were necropsied to determine the cause of death. Birds which were unable to get food and water were culled. The weight and day of removal of all dead and culled birds was recorded. The chicks were weighed on Day 21 and Day 46 of the study. Feed efficiency was determined by dividing the amount of feed, in pounds, which the chicken consumed by the weight it gained, again in pounds. The results of the study at Day 21 are reported in Tables III, IV and V are illustrated in FIG. 5. Results at Day 46 are reported in Tables VI, VII and VIII and illustrated in FIG. 5. A statistical analysis of the results employing Duncan's New Multiple Range Test is presented in Table IX.

TABLE III

| Pen | Test/Control | Avg Bird Wt (lbs) | Feed/Gain |
|---|---|---|---|
| 65 | Test | 1.184 | 1.366 |
| 66 | Test | 1.129 | 1.380 |
| 67 | Test | 1.205 | 1.358 |
| 68 | Test | 1.194 | 1.363 |
| 69 | Test | 1.216 | 1.368 |
| 70 | Test | 1.228 | 1.371 |
| 72 | Test | 1.290 | 1.364 |
| 64 | Control | 1.177 | 1.392 |
| 63 | Control | 1.130 | 1.388 |
| 53 | Control | 1.141 | 1.383 |
| 27 | Control | 1.062 | 1.419 |
| 30 | Control | 1.130 | 1.406 |
| 18 | Control | 1.103 | 1.385 |
| 71 | Control | 1.186 | 1.452 |

TABLE IV

SUMMARY OF DATA

| | AVG BODY WT (lbs) DAY 21 | AVG FEED/GAIN DAY 21 |
|---|---|---|
| Control | 1.133 | 1.404 |
| Test | 1.206 | 1.367 |

TABLE V

ANALYSIS OF VARIANCE

| | DF* | SS** | MS*** | F**** |
|---|---|---|---|---|
| 21 DAY BODY WEIGHT | | | | |
| Treatment | 1 | 0.0199 | 0.01909 | 13.30856 |
| Replication | 6 | 0.01635 | 0.00273 | 1.89955 |
| Error | 6 | 0.00861 | 0.00143 | |
| Total | 13 | 0.04406 | | |
| 21 DAY FEED/GAIN | | | | |
| Treatment | 1 | 0.00465 | 0.00465 | 12.14572 |
| Replication | 6 | 0.00173 | 0.00029 | 0.75371 |
| Error | 6 | 0.00230 | 0.00038 | |
| Total | 13 | 0.00867 | | |

*Degrees of Freedom
**Sum of Squares
***Standard Error of Mean
****Assessment of Significance

TABLE VI

| Pen | Test/Control | Avg Bird Wt (lbs) | Feed/Gain |
|---|---|---|---|
| 65 | Test | 4.970 | 1.902 |
| 66 | Test | 4.868 | 1.879 |
| 67 | Test | 4.672 | 1.936 |
| 68 | Test | 4.803 | 1.896 |
| 69 | Test | 4.908 | 1.925 |
| 70 | Test | 4.941 | 1.824 |
| 72 | Test | 4.820 | 1.859 |
| 64 | Control | 4.669 | 1.921 |
| 63 | Control | 4.695 | 1.933 |
| 53 | Control | 4.415 | 1.996 |
| 27 | Control | 4.205 | 1.924 |
| 30 | Control | 4.800 | 1.933 |
| 18 | Control | 4.586 | 1.901 |
| 71 | Control | 4.738 | 1.909 |

TABLE VII

SUMMARY OF DATA

| | AVG BODY WT (lbs) DAY 21 | AVG FEED/GAIN DAY 21 |
|---|---|---|
| Control | 4.587 | 1.931 |
| Test | 4.854 | 1.889 |

TABLE VIII

ANALYSIS OF VARIANCE

| | DF* | SS** | MS*** | F**** |
|---|---|---|---|---|
| 46 DAY BODY WEIGHT | | | | |
| Trtmnt | 1 | 0.25089 | 0.25089 | 16.11932 |
| Repl | 6 | 0.22965 | 0.03827 | 2.45906 |
| Error | 6 | 0.09339 | 0.01556 | |
| Total | 13 | 0.57393 | | |
| 46 DAY FEED/GAIN | | | | |
| Trtmnt | 1 | 0.00627 | 0.006272 | 20.78077 |
| Repl | 6 | 0.01290 | 0.002157 | 7.12865 |
| Error | 6 | 0.00181 | 0.00030 | |
| Total | 13 | 0.02097 | | |

*Degrees of Freedom
**Sum of Squares
***Standard Error of Mean
****Assessment of Significance

TABLE IX

PROBABILITY LEVEL = 0.05

| TREATMENT | MEAN | SIGNIFICANCE |
|---|---|---|
| Control-Avg Body Wt, 21 day | 1.133 | B |
| Enzyme-Avg Body Wt, 21 day | 1.206 | A |
| Control-Avg Feed/Gain, 21 day | 1.404 | A |
| Enzyme-Avg Feed/Gain, 21 day | 1.367 | B |
| Control-Avg Body Wt, 46 day | 4.587 | B |
| Enzyme-Avg Body Wt, 46 day | 4.854 | A |
| Control-Avg Feed/Gain, 46 day | 1.931 | A |
| Enzyme-Avg Feed/Gain, 46 day | 1.889 | B |

What is claimed is:

1. A feed composition comprising (A) protein, vitamins and minerals; (B) a source of carbohydrates, comprising a mannan-containing hemicellulose selected from the group consisting of soybeans, corn, and alfalfa; and (C) a mannanase that catalyzes the degradation of said mannan-containing hemicellulose, where the addition of said mannanase decreases the ratio of feed to gain, or increases weight gain, during growth of an animal fed said feed composition, relative to said animal fed on an identical feed composition absent said mannanase.

2. A feed composition according to claim 1, wherein said mannanase is a *Bacillus mannanase*.

3. A feed composition according to claim 1, wherein said group consists of soybeans and alfalfa.

4. A feed composition according to claim 1, wherein said composition is for a monogastric animal.

5. A feed composition comprising soybean meal and a mannanase component that decreases the ratio of feed to gain, or increases weight gain, during growth of an animal fed said feed composition, relative to said animal fed an identical feed composition absent said mannanase.

6. A feed composition according to claim 5, wherein said mannanase is a *Bacillus mannanase*.

7. A nutritive method for a monogastric animal, comprising the steps of (A) preparing a feed composition comprised of protein, vitamins and minerals, and further comprising a carbohydrate source comprised of mannan-containing hemicellulose selected from the group consisting of soybeans, corn, and alfalfa; and (B) incorporating into said composition a mannanase that catalyzes the degradation of said mannan-containing hemicellulose, where the addition of said mannanase decreases the ratio of feed to gain, or increases weight gain, during growth of an animal fed said feed composition, relative to said animal fed on an identical feed composition absent said mannanase.

8. A method according to claim 7, wherein said group consists of soybeans and alfalfa.

9. A method according to claim 7, wherein step (B) comprises (i) producing a mixture containing said mannanase and said composition and then (ii) pelletizing said mixture under conditions including temperatures of at least 60° C.

10. A method according to claim 9, wherein said carbohydrate source is soybeans.

* * * * *